(12) United States Patent
Withington et al.

(10) Patent No.: US 6,710,706 B1
(45) Date of Patent: Mar. 23, 2004

(54) SPATIAL AWARENESS DEVICE

(75) Inventors: Deborah Jane Withington, Leeds (GB); Dean Andrew Waters, Leeds (GB); Malcolm James William Povey, Leeds (GB); Brian Stewart Hoyle, Leeds (GB)

(73) Assignee: Sound Foresight Limited, Warrington (GB)

( * ) Notice: Subject to any disclaimer, the term of this patent is extended or adjusted under 35 U.S.C. 154(b) by 0 days.

(21) Appl. No.: 09/581,083

(22) PCT Filed: Dec. 1, 1998

(86) PCT No.: PCT/GB98/03589

§ 371 (c)(1),
(2), (4) Date: Aug. 17, 2000

(87) PCT Pub. No.: WO99/29276

PCT Pub. Date: Jun. 17, 1999

(30) Foreign Application Priority Data

Dec. 9, 1997 (GB) .............................................. 9726014

(51) Int. Cl.[7] .................................................. H04B 3/36
(52) U.S. Cl. ..................... 340/407.1; 367/116; 434/112
(58) Field of Search ........................ 340/407.1; 342/24; 367/116; 434/112

(56) References Cited

U.S. PATENT DOCUMENTS

| 3,654,477 | A | | 4/1972 | Benjamin, Jr. ....... 340/407.1 X |
|---|---|---|---|---|
| 4,212,258 | A | | 7/1980 | Collins ........................ 114/312 |
| 4,823,657 | A | | 4/1989 | Welin-Berger ............... 82/162 |
| 4,982,432 | A | * | 1/1991 | Clark et al. .................... 381/41 |
| 5,388,992 | A | | 2/1995 | Franklin et al. ......... 434/112 X |
| 5,807,111 | A | | 9/1998 | Schrader ..................... 434/112 |
| 5,816,277 | A | * | 10/1998 | Jansen .......................... 135/65 |
| 5,982,286 | A | * | 11/1999 | Vanmoor ................. 340/573.4 |

FOREIGN PATENT DOCUMENTS

| DE | 19525010 | | 1/1987 |
|---|---|---|---|
| DE | 9415210 | | 12/1994 |
| DE | 4402764 | A1 * | 7/1995 |
| EP | 0167471 | | 4/1985 |
| EP | 0774245 | | 11/1996 |
| WO | 95/21595 | | 8/1995 |
| WO | 97/15265 | | 5/1997 |

* cited by examiner

Primary Examiner—Thomas Mullen
(74) Attorney, Agent, or Firm—Jacobson Holman PLLC

(57) ABSTRACT

A spatial awareness device comprising at least one receiver adapted to receive a selected form of radiation and operatively coupled thereto at least one tactile responsive element. The received radiation can be converted into a tactile map spanning at least in part a limb of an individual such as a hand or foot.

20 Claims, 5 Drawing Sheets

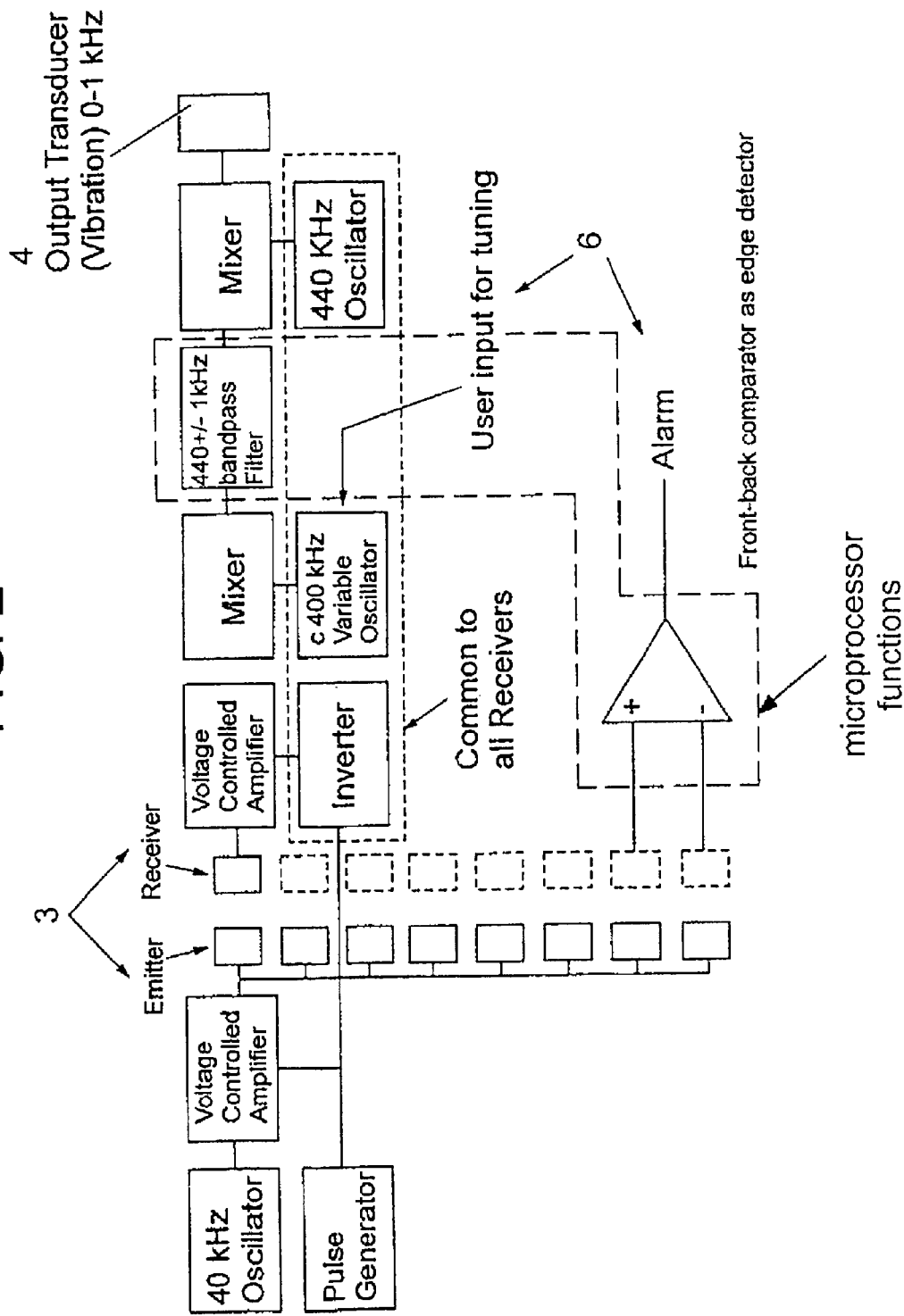

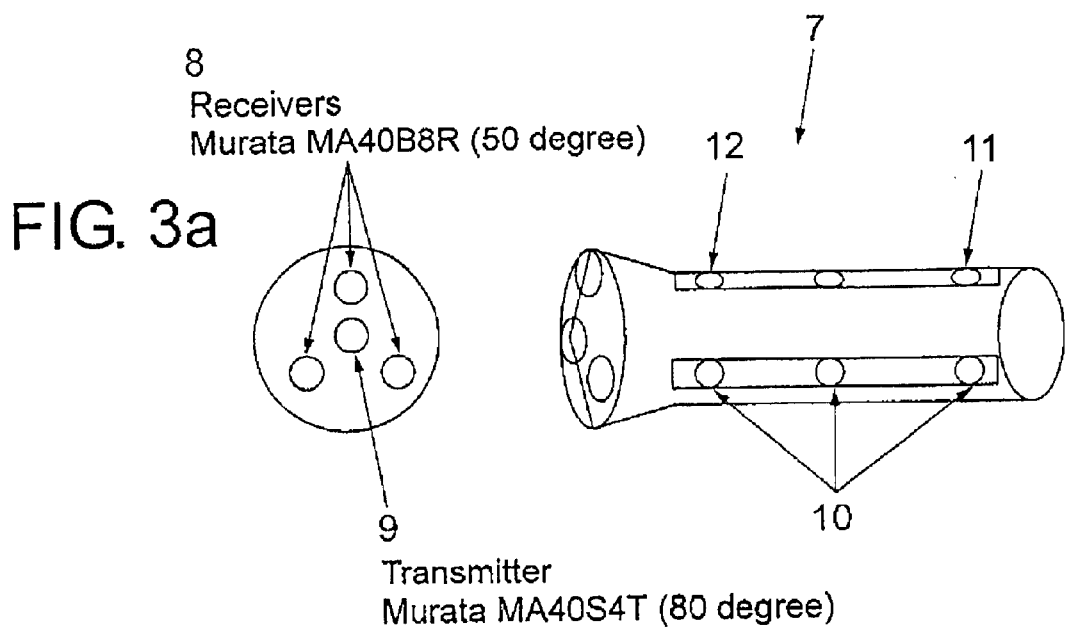
FIG. 3a
8
Receivers
Murata MA40B8R (50 degree)
9
Transmitter
Murata MA40S4T (80 degree)
FIG. 3b
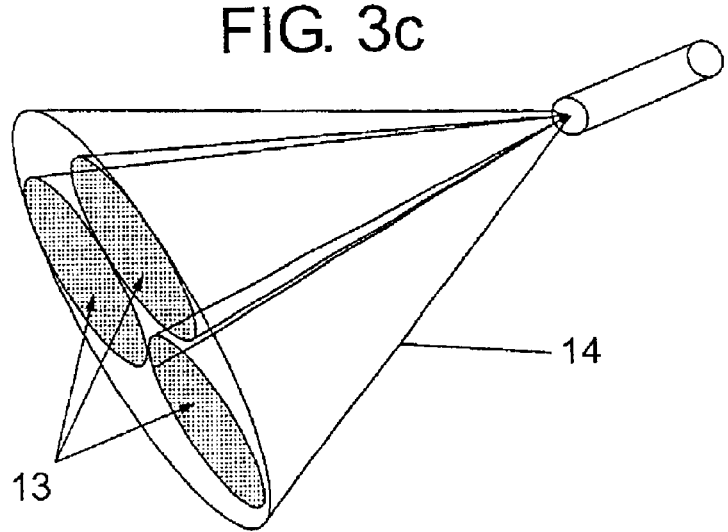
FIG. 3c

SPATIAL AWARENESS DEVICE

FIELD OF THE INVENTION

The invention relates to a Spatial Awareness Device for individuals whose vision or hearing may be impaired or lost, either due to physical abnormalities/disability or due to a sensory derived environment for example in darkness, fog or underwater locations.

BACKGROUND OF THE INVENTION

There are a number of guiding or locating devices for visually impaired or blind individuals, for example the guiding device described in EP 749744. This guiding device is built in two parts. One part includes a receiver and a transmitter and the other part includes a microprocessor for processing the signals received from the receiver. Additionally, the second part includes a mechanical signal generator. Typically the second part is held in a blind person's breast pocket. The transmitter emits ultrasound waves which are reflected by an obstacle. The reflective signal activates the mechanical device thus warning a user about the presence of the obstacle. The guide thus acts a proximity warning device, notably, it does not provide information in the form of a picture about the surrounding environment and what is more, it is still necessary for the blind person to use a stick to detect holes in the ground, curb edges and stairs.

Dutch Patent NL 9301911 describes a stick for the blind or partially sighted which includes a handle into which there is incorporated a radio transmitter and a receiver. The transmitter and receiver use ultrasound, infra red or microwave radar signals to detect objects in the path of the user. The received signal is processed and used to drive a motor which in turn alters the position of a small rod protruding from the handle. A user can learn to detect distance of a nearby obstacle by monitoring the movement of the rod.

The advantage of this device is that the proximity detector and the stick are combined. However, notably, the device provides no information in the form of a picture about the surrounding environment.

Similarly, German Patent DE 2932659 also describes a walking stick for the blind into which there is built an ultrasound distance measuring system. The handle of this stick is provided with a distance range adjustment means comprising a finger operated ratchet lever. The lever can be adjusted in order to adjust the range of the ultrasound system. Using this device an individual can determine at what distance objects are to be detected. However, noticeably, this device does not provide any detailed information of the environment in which the individual is located.

In addition, each of the above devices are only for use by visually impaired or blind individuals; they are not for use by partially deaf or deaf individuals or for individuals navigating sensory deprived environments. Further they only relay limited information about the immediate environment (a radius of approximately 1 m).

It can then be seen that there is a need to provide a device which provides an individual with relatively detailed information about the environment they occupy and more specifically a single device that will provide a visually impaired or blind individual with information about the spatial content of their environment and a partially deaf or deaf individual with information about the distance and direction of different sounds within their environment. There is also a need to provide individuals in sensory deprived environments with such information.

SUMMARY OF THE INVENTION

It is therefore an object of the invention to provide a device which overcomes the problems associated with the prior art and fulfills the aforementioned needs.

According to a first aspect of the invention there is therefore provided a spatial awareness device comprising at least one receiver for receiving a selected form of radiation and operatively coupled thereto at least one tactile responsive means; whereby the radiation can be converted into a tactile map spanning at least in part the body of an individual.

Indeed, it is known that the human central nervous system (CNS) contains "brain maps" of the visual/auditory and somatosensory (tactile) world. The brain is organised such that these maps of the different sensory modalities interact with one another and changes in one sense may impinge on another modality map. Loss of vision, for example in the congenitally blind, may result in the visually impaired having poor auditory spatial ability. Nevertheless, the majority of vision loss occurs in later life thus all the spatial maps have been created in the CNS.

Utilising spatial tactile sensations will use the region of the brain used for visual spatial maps and, more importantly, will use the same cells responsible for auditory localization. Thus, by utilising more than one sensory modality, the user's spatial awareness can be enhanced. This can be useful, for example for effective negotiation or awareness of one's surroundings.

Radiation may be received from sources in the environment or transmitted from the device itself. Preferably, the spatial awareness device also comprises at least one transmitter adapted to transmit the selected form of radiation; the receiver being adapted to receive the reflected radiation. In this way, reflected radiation from objects in the environment can form the tactile map. It is preferred that the transmitter and receiver transmit and receive electromagnetic or acoustic radiation.

In a more preferred embodiment of the invention the selected form of radiation is ultrasound however, in alternative embodiments of the invention the radiation may be infra red radiation or microwave radar signals.

Where the radiation is both transmitted and received, it is preferred that the electromagnetic radiation or acoustic radiation is selected so as not to interfere with sounds in the human hearing range so as to avoid cutting off an additional primary sense in particular for use by the visually impaired or blind.

In a further preferred embodiment of the invention said tactile responsive means is controlled by a control means such as a microprocessor adapted to receive information from the receiver about the received radiation. More preferably, it converts said information, preferably by way of stepping down the frequency, so that the received echo can be turned into a tactile signal, ideally a vibration, which an individual can feel through the tactile responsive means.

More preferably still, the control means is programmed so that the position of the tactile signal on the tactile responsive means, and corresponding part of the user's body, provides information about the location of an obstacle in the spatial environment. In this way, a spatial map is created across the body, such as across the palm of the hand.

Additionally or alternatively, the strength of the tactile signal may be controlled by the control means so as to provide information about the size of an obstacle in the spatial environment. Thus, in the instance where ultrasound is used, the reflection of ultrasound from a nearby obstacle will be relatively great compared to the reflection of ultrasound from a distant obstacle, and so the strength of the ultrasound echo can be directly correlated with the strength of the tactile signal or vibration providing information on the body not only about the relative location of one obstacle with respect to another but also the relative proximity to the user of one obstacle with respect to another. Thus the tactile signal may be graded to give object proximity, or even object density information, since the density of a given object will affect the nature of the reflected radiation.

The device may be fixed or mobile. Preferably the spatial awareness device is mobile and may be used to span the body at any part which is sensible to tactile sensation such as a hand, foot, back, limb or portions thereof. It may even cover a substantial part of the body surface, for example in the form of a body suit. The device may alternatively be hand-held, for example, in the form of a torch or it may be provided as a back pack or front pouch.

In a further preferred embodiment of the invention said tactile responsive means comprises a shield, knob, plate or pad of selected ergonomic configuration. Preferably the device has an ergonomically favoured configuration which may be selected to sit within the palm of the hand and ideally running along the fingers and especially the fingertips or across the entire underside of the hand.

In another preferred embodiment of the invention the hand held device may be incorporated into a glove. The device may be water resistant so that it can be used under water by divers diving either in obscure or deep water.

Ideally, spatial mapping is performed by providing a plurality of paired transmitters and receivers each pair designed to project selected radiation so as to cover a selected angular field or "field of view". Information from each pair of transmitters and receivers can then be processed by the control means and sent to a specific region of the tactile responsive means.

Additionally, or alternatively, a single transmitter and receiver adapted to cover a relatively wide angular field or "field of view" is provided and the information from the single receiver is fed into a control means adapted to process information from this relatively wide angular field and then map the processed information to specific parts of the tactile responsive means thus providing a spatial map of the surrounding environment.

Additionally, or alternatively further still a single wide beam transmitter is used to transmit said electromagnetic radiation or acoustic radiation but a plurality of receivers are provided with a view to resolving spatial ambiguities.

It will be apparent to those skilled in the art of the provision of mobile devices that such a device is advantageous because it enables the user to selectively "view" the spatial environment by directing the hand or other body portion within that environment.

Moreover, it will be apparent to those skilled in the art that the effect of the Doppler shift on electromagnetic radiation or acoustic radiation will also provide information about the movement of obstacles within the environment. Thus, depending upon whether or not an object is moving towards or away from the device, the electromagnetic radiation or acoustic radiation patterns will be effected and will effect whether the tactile signal grows or diminishes in intensity over a period of time. Therefore it follows that an individual standing still within an environment can use the device to determine the location of obstacles in the environment and moreover to distinguish between obstacles that are stationary and those that are moving. Clearly, as an individual learns to use the device it will be possible for the individual to learn to move with the device in the environment and to distinguish relative movement i.e. movement of an individual towards or away from a stationary object and movement of an individual towards or away from a moving object. It will be apparent that the individual will be learning to recognise not only the mapping of signals on the hand but also changes in the intensity of those signals.

Additionally, the tactile signal may be mapped to a specific location on the mobile device so that an individual hard of hearing can determine from which part of his/her environment the sound originates. Moreover, the control means is also adapted to correlate the intensity or loudness of the sound with the intensity or strength of the tactile response. Thus for example, particularly loud noises will provide particularly strong tactile responses in particular regions of the tactile responsive means. Alternatively, a quieter sound will provide a smaller tactile sensation in a particular region of the tactile responsive means. In this way an individual can use the spatial awareness device to obtain information about objects or sounds within the spatial environment.

In yet a further preferred embodiment of the invention the device is adapted to switch between the spatial awareness device providing information about the visual environment and the one providing information about the auditory environment.

In yet a further preferred embodiment of the invention said spatial awareness device may be provided as a pair of devices, one adapted to map to a left part of the body and one adapted to map to a right part of the body.

Advantageously, the pair of spatial awareness devices may be provided wherein one provides information about the visual environment and the other provides information about the auditory environment.

Alternatively yet again the pair of spatial awareness devices may be provided wherein one of said devices provides information about a first lateral or remote "field of view" and the other of said devices provides information about a second, opposite, lateral or proximal "field of view".

In a further aspect, the invention provides the use of a device as hereinbefore defined to determine the location of obstacles and/or sounds in the environment and to distinguish between obstacles and/or sounds that are stationary and those that are moving.

In a yet further aspect there is provided according to the invention a method for negotiation or awareness of an environment comprising associating a device as hereinbefore defined with an individual such that it spans at least a part of the individual's body and detecting radiation via the device.

In a yet further aspect there is provided a kit of parts forming a spatial awareness device as hereinbefore defined.

An embodiment of the invention will now be described by way of example only.

In the following description of the invention conventional circuitry and devices are used to build the spatial awareness device.

In one of its simplest forms the spatial awareness device comprises an ergonomically fashioned pad which is adapted to sit within the palm of a user's hand. The pad is provided with attachment means whereby the pad can be attached using straps or the like typically attached about the wrist or fingers of a hand. The side of the pad adjacent the palm may take one of two forms. It may be provided with protuberances which are adapted to move or vibrate upon activation; the frequency of the vibration being determined by the strength of the activating signal. Alternatively, said surface may be smooth but adapted over discrete regions to emit very small, but detectable, electric signals so that a wearer feels a tingling sensation when the pad is activated; the strength of the tingling sensation being determined by the strength of the activation.

On the side of the pad facing outwardly and thus towards the environment there is provided at least one ultrasound transmitter and one ultrasound receiver. The "field of view" of the transmitter and receiver is selected so as to provide as much useful information about the environment as possible and is, for example, in the order of 3–4 metres. Additionally, initiation and control means may be provided so that a user can initiate the device and also preferably alter the size of the "field of view".

Embedded within the pad is a control means in the form of a microprocessor which is connected to both the transmitter, receiver and tactile responsive side of the pad using conventional circuitry. Moreover, the microprocessor is provided with means suitable for altering the frequency of the echoed ultrasound and thus stepping down the frequency so as to produce a tactile signal that is able to either vibrate the tactile protuberances or be converted into an electrical signal, using conventional means, in order to provide a small, but detectable, electrical signal.

BRIEF DESCRIPTION OF THE DRAWINGS

Embodied within the microprocessor is both a map of the tactile responsive means and a map of the surrounding environment derived from the ultrasound echo. Thus the microprocessor is adapted to direct information from the environment, or ultrasound echoes, to a specific part of the tactile responsive means and so ensure that spatial mapping is achieved. The circuitry and processing for undertaking this mapping is conventional.

In an alternative embodiment of the invention the receiver is adapted to receive sound waves within the human hearing range and the microprocessor is adapted to map these sound waves to specific parts of the tactile responsive means. Thus in this alternative embodiment of the invention an auditory map of an individual's environment is provided. Again, conventional circuitry and processing means are used in this embodiment.

Embodiments of the invention are shown, by way of example, with reference to FIGS. 1–4, wherein.

FIG. 2 is a diagrammatic illustration of the circuitry used in the FIG. 1 embodiment;

FIG. 3 is a diagrammatic illustration of an alternative embodiment of the invention;

FIG. 3a shows the embodiment in front view, FIG. 3b in side view and FIG. 3c in use;

DETAILED DESCRIPTION OF PREFERRED EMBODIMENTS

Figure 1:
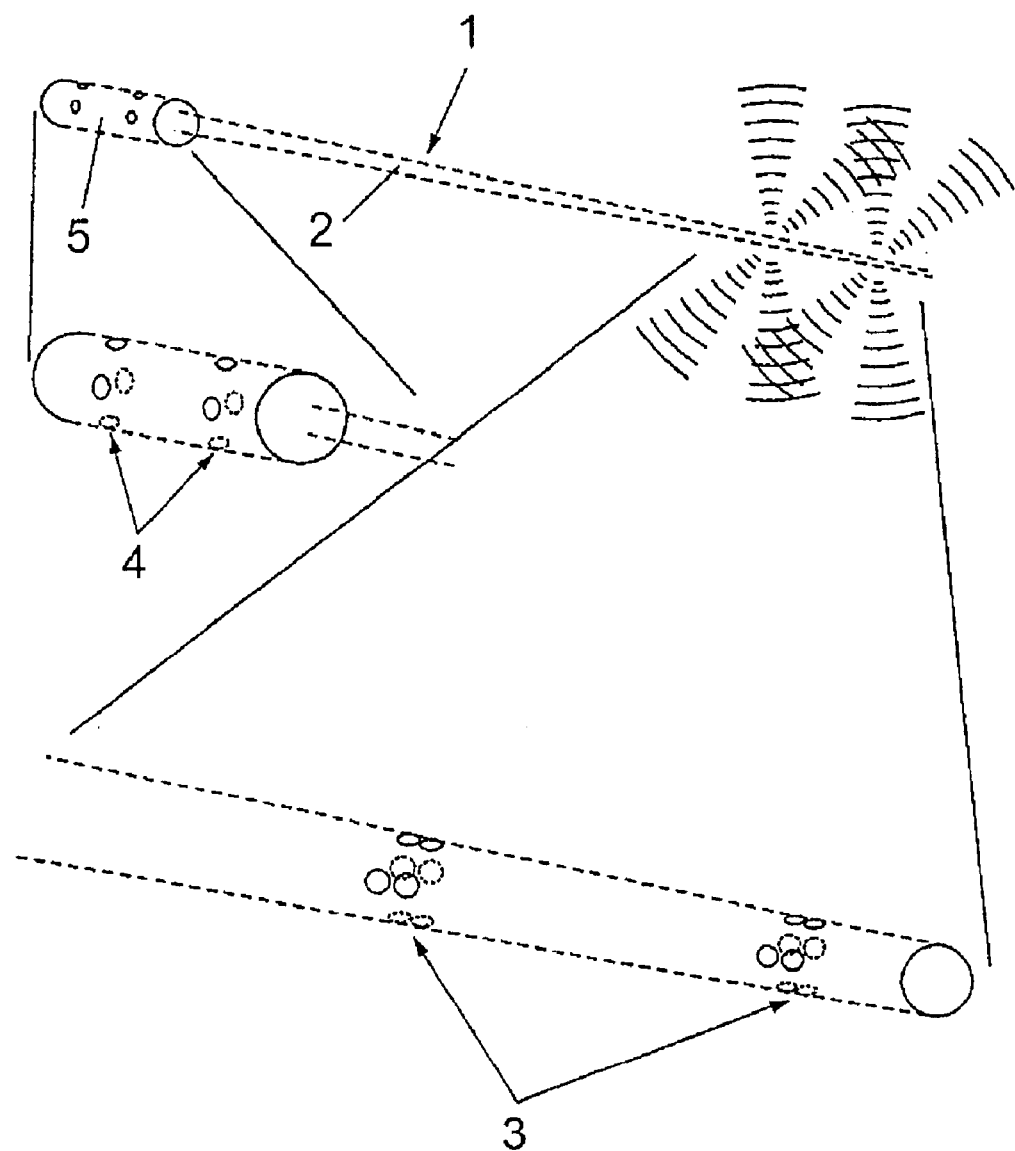
FIG. 1 is a diagrammatic illustration of an embodiment of the invention.

FIG. 1 shows a hand-held spatial awareness device (1) embodied within the handle of a white stick (2). At the end of the stick (2) further from the user, emitter/receiver pairs (3) are provided. Reflected ultrasound radiation is received by the receivers and processed via control means (6) which control tactile responsive means at end (5), shown as an array of Piezo electric transducers (4). These produce vibration in response to signals from the control means, the location and extent of the vibration corresponding to the size and location of objects detected in the environment. The transducers are mounted in a stiff material allowing good transmission of vibrations.

FIG. 2 shows the control means (6) and its connections to the emitter/receiver pairs (3) and the Piezo electric transducers(4). Ultrasound at 40 khz is produced by an oscillator. This signal is fed with amplification and pulse generation to the emitter. The same pulse generator gates a superheterodyne receiver preferably of at least 5 mm diameter, allowing high gain with good signal to noise ratio. The reflected signal is then relayed to Piezo electric transducer (4).

FIG. 2 also shows a front-back comparator which is provided on the underside of the strip to compare front-back amplitudes. This is for use as an edge detector.

FIG. 3a, b and c shows a hand-held spatial awareness device (1) embodied within a torch (7). Vibrations are transmitted along the length of the torch handle to an array of vibrating couplers (10) forming the tactile responsive means. Depending on the pulse-echo time a timer increases or decreases the amplitude of vibrations to each of the actuators, moving the peak signal to a far indicator (11) at the base of the torch for a distant object and to a close indicator (12) at the front for a close object. The receiver receives distance information in the form of amplitude related cues as well as spatial mapping cues.

FIG. 3a demonstrates the positioning of the single transmitter having a wide transmission field such as 75° or 80° with respect to a plurality of receivers each have an approximately 40° receiver field.

FIG. 3c demonstrates the transmitter field (14) and receiver fields (13) in use.

Figure 4:
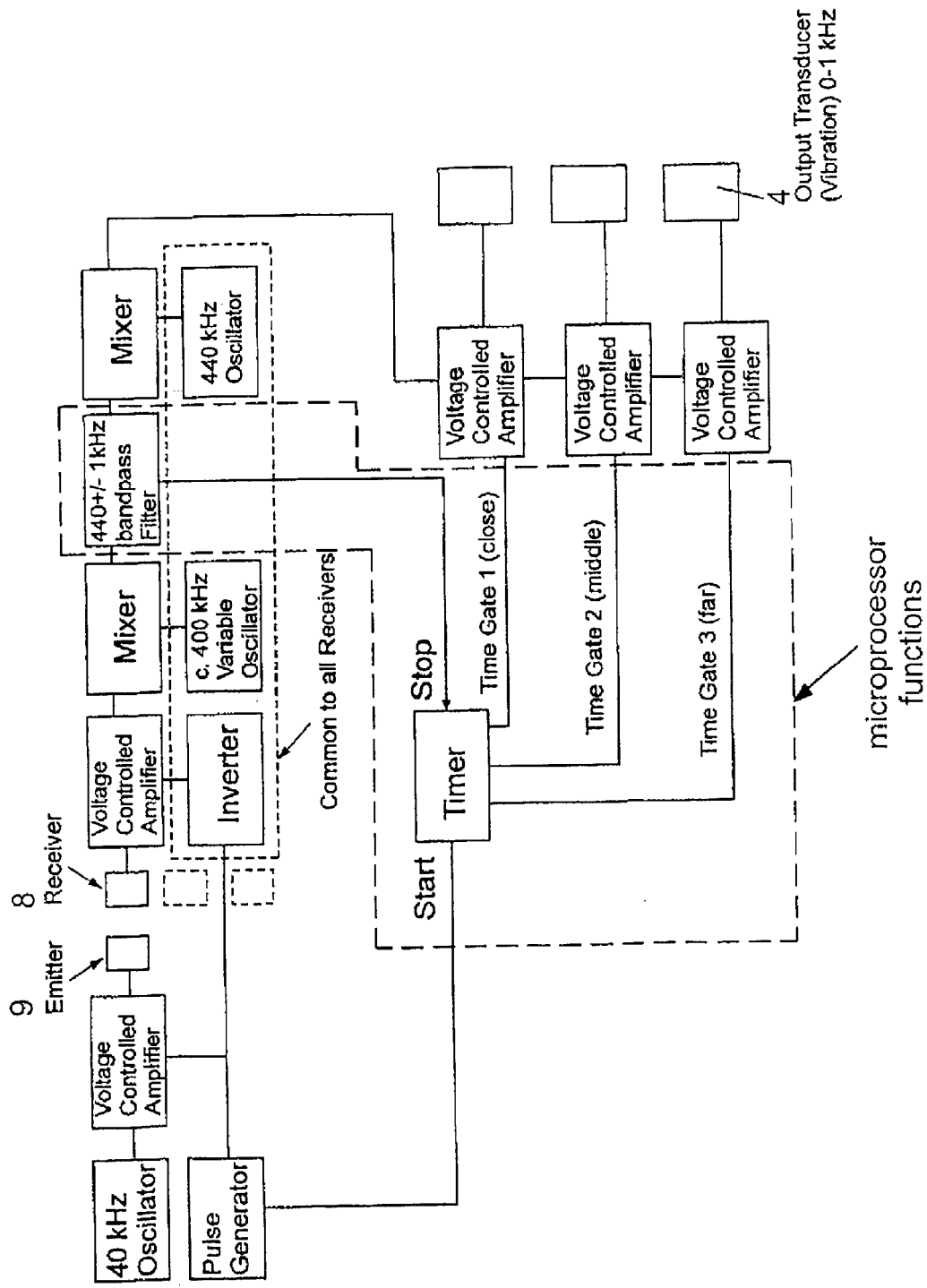
FIG. 4 is a diagrammatic illustration of the circuitry used in the FIG. 3 embodiment.

FIG. 4 illustrates the control means which uses similar components to those used in the previous embodiment. However, in this instance, the receiver would also sense the peak echo, switching off a timer. Depending on the pulse-echo time, the timer would increase or decrease the amplitude of the vibration to each of the transducers (4), moving the peak signal to the base of the torch for a distant object and to the front for a close object.

Figure 5:
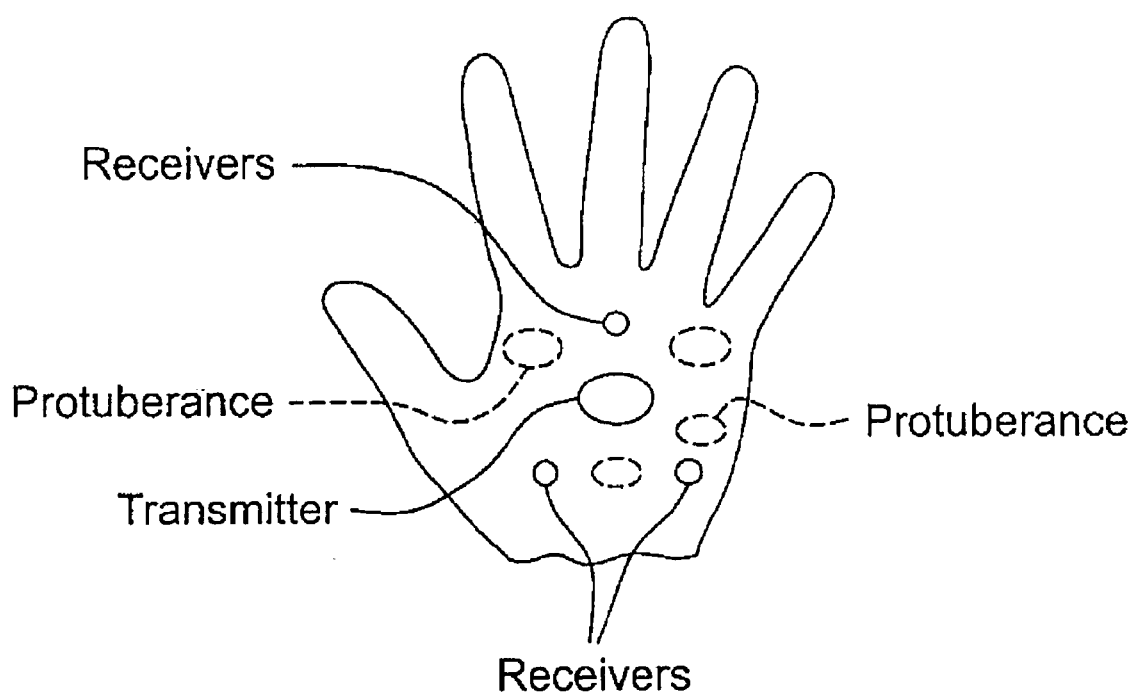
FIG. 5 shows a glove including the transmitting and receiving transducers.

FIG. 5 illustrates a glove in accordance with the present invention showing the transmitter and receivers on the glove and tactile responsive protuberances at the side of the glove in contact with a user's hand.

Figure 6:
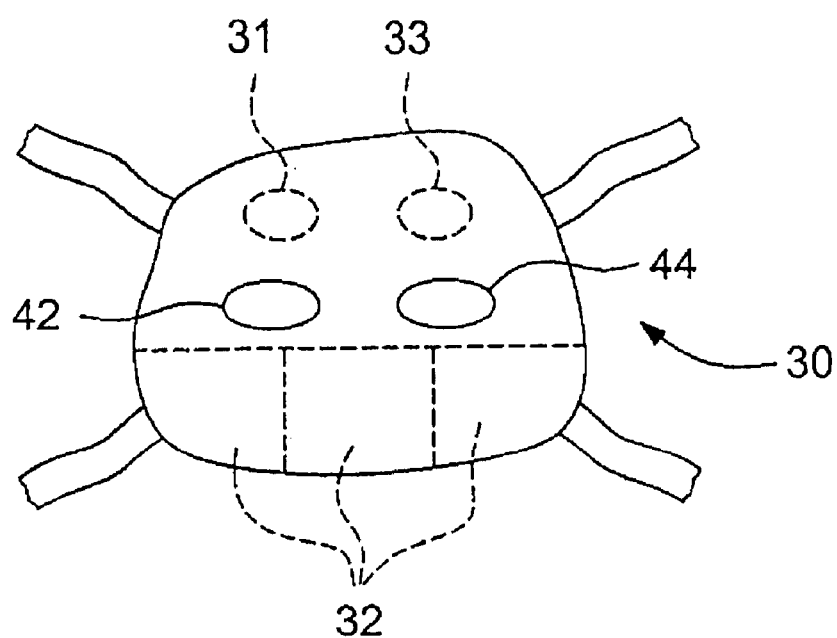
FIG. 6 shows a pad for attachment to a limb of a user such as the palm of a user's hand.

FIG. 6 discloses a pad 3 having a transmitter 42 and a receiver 44. As described above the pad may be attached to the palm of a user. Protuberances 31 and 33 are in contact with the palm. Alternatively, discrete regions 32 may be provided. It should be apparent that this pad could be used on any limb including the foot of a user.

It can therefore be seen that the invention provides a unique way in which individuals who are either visually impaired or blind and/or partially deaf or deaf can obtain information about their spatial environment.

What is claimed is:

1. A spatial awareness device comprising at least one ultrasound transmitter for transmitting ultrasound radiation over a wide angular field within a spatial environment surrounding the device, at least one ultrasound receiver for receiving ultrasound radiation over a wide angular field reflected from obstacles located in the spatial environment, at least one control means responsive to the received ultrasound radiation from said at least one ultrasound receiver, at least one tactile responsive means operatively coupled to said control means and contacting portions of a limb of an individual user, wherein said control means spatially resolves and converts received radiation into a tactile signal such that the position of a signal on the tactile responsive means provides information about the location of an obstacle in the spatial environment surrounding the device, said tactile signal spatially distributed across at least portions of said limb of an individual user to stimulate in a user spatial tactile sensations thereon.

2. A spatial awareness device according to claim 1 wherein the control means comprises a microprocessor programmed to convert reflected ultrasound into a spatial map on the tactile responsive means.

3. A spatial awareness device according to claim 1 wherein the tactile responsive means comprises a plurality of protuberances adapted to move or vibrate on activation to produce a tactile signal.

4. A spatial awareness device according to claim 1 wherein said tactile responsive means comprises an array of piezoelectric transducers to produce a tactile signal.

5. A spatial awareness device according to claim 1 wherein the tactile responsive means comprises a surface adapted over discrete regions to emit an electrical signal.

6. A spatial awareness device according to claim 1 wherein the tactile signal is a vibration.

7. A spatial awareness device according to claim 6 wherein the position of the vibration on the tactile responsive means is controlled by the control means so as to provide information about the angular location of an obstacle in the spatial environment.

8. A spatial awareness device according to claim 6 wherein the position of the vibration on the tactile responsive means is controlled by the control means so as to provide information about the proximity of an obstacle in the spatial environment.

9. A spatial awareness device according to claim 6 wherein the extent of the vibration on the tactile responsive means is controlled by the control means so as to provide information about the size and/or proximity of an obstacle in the spatial environment.

10. A spatial awareness device as claimed in claim 1 further comprising a plurality of paired transmitters and receivers each pair designed to project selected radiation so as to cover a selected angular field.

11. A spatial awareness device as claimed in claim 1 comprising a single transmitter and receiver adapted to cover a relatively wide angular field.

12. A spatial awareness device according to claim 1 wherein said at least one ultrasound transmitter comprises a single wide beam transmitter and at least one ultrasound receiver comprises a plurality of receivers.

13. A spatial awareness device according to claim 1 further comprising at least one receiver for receiving acoustic radiation within the human hearing range and wherein said control means includes means for generating a tactile signal corresponding to the acoustic radiation, said tactile signal mapped to specific parts of the tactile responsive means to create a tactile map so that a user can determine from which part of the environment the sound originates.

14. A spatial awareness device according to claim 13 wherein the control means correlates the intensity of loudness of the sound with the intensity of the tactile response.

15. A spatial awareness device according to claim 13 wherein the device is adapted to switch between providing information about the spatial environment to one providing information about the auditory environment.

16. A spatial awareness device according to claim 1 wherein said tactile responsive means comprises at least one of a shield, knob, plate or pad configured to sit within the palm of the hand of a user, contacting the fingers along their length and/or fingertips and/ or the entire underside of the hand, for stimulating the hand of an individual and for creating a tactile map spanning the hand.

17. A spatial awareness device according to claim 1 wherein said tactile responsive means is incorporated into a glove.

18. A spatial awareness device according to claim 17 wherein the device is water resistant for underwater diving use.

19. A method for negotiating awareness of an environment comprising associating a spatial awareness device as claimed in claim 1 with an individual such that the tactile responsive means spans at least one of the hand, foot, or portions thereof, of an individual, transmitting ultrasound radiation, receiving reflected ultrasound radiation, converting received ultrasound radiation into a tactile signal such that the position of a signal on the tactile responsive means provides information about the location of an obstacle in the spatial environment surrounding the device, said tactile responsive means spatially distributed across at least one of the hand, foot, or portions thereof, of an individual user to stimulate in a user spatial tactile sensations thereon.

20. A method according to claim 19 wherein the control means is operatively coupled to the responsive means such that the strength of the tactile signal on the tactile responsive means, provides information about size and/or location and/or density of an obstacle in the spatial environment.

\* \* \* \* \*